United States Patent [19]
Levius

[11] Patent Number: 5,171,272
[45] Date of Patent: Dec. 15, 1992

[54] FLUID PUMP FOR PENILE PROSTHESIS

[75] Inventor: Dezso K. Levius, Bloomington, Minn.

[73] Assignee: American Medical Systems, Inc., Minnetonka, Minn.

[21] Appl. No.: 587,139

[22] Filed: Sep. 24, 1990

[51] Int. Cl.⁵ ............................ A61F 2/04; A61F 5/00
[52] U.S. Cl. ........................................ 623/12; 600/40
[58] Field of Search ................... 128/79, 79 A; 623/12

[56] References Cited

U.S. PATENT DOCUMENTS

| | | | |
|---|---|---|---|
| 4,523,584 | 6/1985 | Yachia et al. | 128/79 A |
| 4,566,446 | 1/1986 | Fogaraty | 128/79 A |
| 4,604,994 | 8/1986 | Sealfon | 128/79 A |
| 4,665,903 | 5/1987 | Whitehead | 623/12 |
| 4,766,889 | 8/1988 | Trick et al. | 128/79 A |
| 4,782,826 | 11/1988 | Fogarty | 128/79 A |
| 5,101,813 | 4/1992 | Trick | 600/40 |

FOREIGN PATENT DOCUMENTS 0065853 12/1982 European Pat. Off. .
2192546 1/1988 United Kingdom .

Primary Examiner—David Isabella
Attorney, Agent, or Firm—Peter C. Richardson; Lawrence C. Akers; Thomas C. Naber

[57] ABSTRACT

A hand operable, two-component fluid pump for inflating an inflatable penile prosthesis. The pump comprises a high-volume, low-pressure first pump component and at least one low-volume, high-pressure second pump component. Fluid to be pumped to the prosthesis is housed within the first component, and each of the first and second components is in valved communication with the prosthesis and in valved communication with each other. In a preferred embodiment the second pump component is disposed within the first pump component. The pump preferably can be implanted within the user, with the most preferable implantation site being within the scrotal sack.

6 Claims, 1 Drawing Sheet

FLUID PUMP FOR PENILE PROSTHESIS

BACKGROUND OF THE INVENTION

This invention relates in general to fluid pumps, and in particular to a two-component fluid pump for inflation of a penile prosthesis, wherein one pump component is low pressure and high volume while the other component is high pressure and low volume.

The use of penile prosthetic devices to alleviate problems of impotence is widely recognized. One general type of device comprises a pair of inflatable cylinders which are implanted within the penis and which are in communication with a source of fluid. This fluid is pumped into the cylinders as desired by the user in order to produce a penile erection. In one type of arrangement the fluid itself can be in a reservoir which can be situated inside the abdominal cavity of the user, with the reservoir being in communication with a pump means for delivering the fluid from the reservoir to the prosthetic device. Alternatively, the fluid can be wholly stored within a pump means for introduction into the prosthetic device as desired. A present pump means for either type of arrangement generally is scrotally implanted and is comprised of a single, hollow, flexible component having a ball valve through which the fluid must pass for entry into the cylinders of the prosthesis. Fluid within the component is pumped through the ball valve by repeatedly squeezing the component until a majority of the fluid has left and entered the cylinders. The user can cause the return of the fluid to the component by squeezing the site of the ball valve to thereby displace the ball and allow fluid to flow back into the component. As is apparent, however, the size of the component must be large enough to accommodate the amount of fluid required to satisfy the cylinders of the prosthetic device. This resultant high-volume component necessarily delivers fluid at low pressure and, because of its size, does not permit the user to transfer the full amount of fluid present into the cylinders.

In view of the above, it is a primary object of the present invention to provide a two-component prosthesis pump whereby the first component thereof provides for high-volume, low-pressure pumping and the second component thereof provides for subsequent low-volume, high-pressure pumping to thereby increase fluid delivery to the prosthetic device. Another object of the present invention is to provide such a two-component pump wherein the second component thereof is situated within the first component. Yet another object of the present invention is to provide such a two-component pump whereby the pump can be implanted within the scrotum of the user. These and other objects of the invention will be apparent throughout the description which now follows.

SUMMARY OF THE INVENTION

The present invention is a hand operable, two-component fluid pump for inflating an inflatable penile prosthesis. The pump comprises a high-volume, low-pressure first pump component and at least one low-volume, high-pressure second pump component. Fluid to be pumped to the prosthesis is housed within the first component, and each of the first and second components is in valved communication with the prosthesis and in valved communication with each other. In a preferred embodiment the second pump component is disposed within the first pump component. The pump preferably can be implanted within the user, with the most preferable implantation site being within the scrotal sack. Because the first pump component provides high volume at low pressure and is the first pump member to be engaged by a user, it provides the prosthesis with a rapid initial fluid fill. Subsequently, because the second pump component provides high pressure and also completely empties residual fluid remaining in the first pump component after employment of the first pump component, operation of the second pump component provides desired rigidity to the prosthesis and thereby accomplishes an erection for the user which closely simulates a natural occurrence.

BRIEF DESCRIPTION OF THE DRAWINGS

A presently preferred embodiment of the invention is illustrated in the accompanying drawings in which.

DETAILED DESCRIPTION OF A PREFERRED EMBODIMENT

Figure 1:
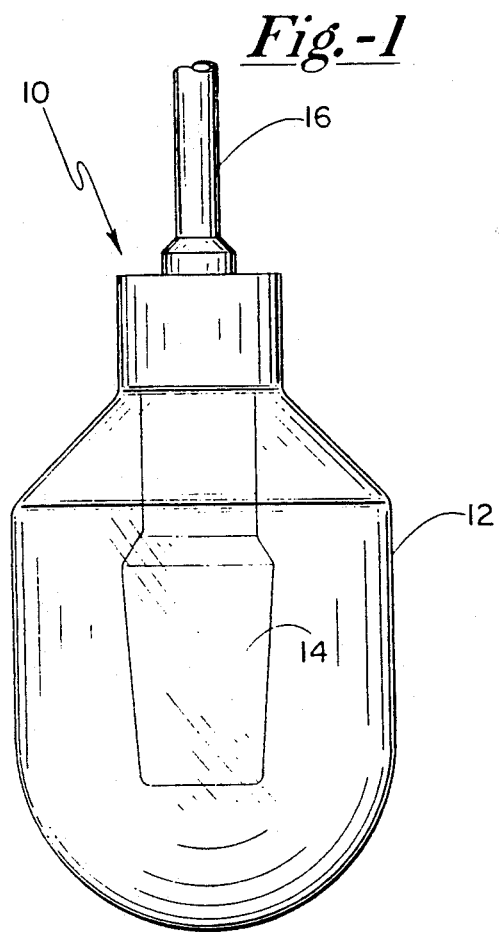
FIG. 1 is a perspective view of a two-component fluid pump for inflating a penile prosthesis.

Referring to FIG. 1, a hand-operable, two-component fluid pump 10 for inflating an inflatable penile prosthesis (not shown) is illustrated. The pump 10 comprises a first pump component 12 and a second pump component 14, with the latter preferably disposed inside the former as here shown. It is to be understood, however, that the second pump component can be disposed outside of the first pump component. The first pump component 12 provides a high volume and a low pressure for pumping fluid therefrom, while the second pump component 14 provides low-volume, high-pressure characteristics. A connector element 16 leads from the pump 10 for coupling with the penile prosthesis. The connector element 16 here shown is for representation only, and can be configured as required so as to provide an effective seal with the prosthesis as recognized in the art. Both pump components 12, 14 are preferably constructed of silicone rubber, with the first component 12 having a volume of from about 12 cc to 25 cc, preferably about 18 cc, and the second component 14 having a volume of from about 2 cc to 4 cc, preferably about 3 cc. The first pump component 12 provides a maximum pressure of about five to seven psi, while the second component 14 provides a pressure of about 10-20 psi. A typical penile prosthesis requires about 10-15 psi for satisfactory rigidity.

Figure 2:
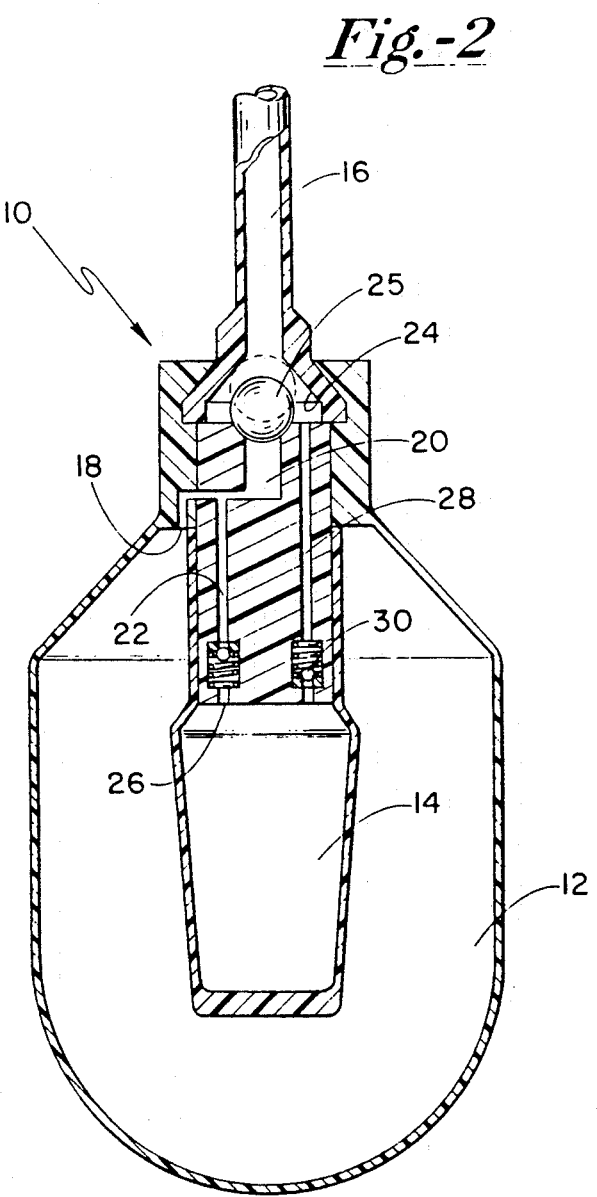
FIG. 2 is an elevation view, in section, of the pump of FIG. 1.

FIG. 2 illustrates the pump 10 in section. The first pump component 12 has leading therefrom a first fluid delivery passage 18 having a first branch 20 and a second branch 22. The first branch 20 leads to the connector element 16 and has disposed therein a ball valve 24 which is displaced and thereby opened by pressurized fluid passing therethrough and traveling to the connector element 16. The second branch 22 leads to the second pump component 14 and has disposed therein a suction valve 26 through which fluid can be drawn for delivery to the second pump component 14. A second fluid delivery passage 28 leads from the second pump component 14 to the connector element 16 and has disposed therein a ball valve 30 which is displaced and thereby opened when fluid under pressure flows therethrough. As is evident from the drawing, the suction valve 26 permits one-way fluid flow from the first pump component 12 to the second pump component 14, while the ball valve 30 permits one-way fluid flow from the second pump component 14 to the connector element 16 as here shown, but can be configured to permit two-way fluid flow if fluid flow from the prosthesis to the second pump component 14 is desired. The ball valve 24 permits two-way fluid flow, depending upon ball disposition as discussed later, between the first pump component 12 and the connector element 16. The walls of both the first and second pump components 12, 14 are flexible and can be constructed of silicone rubber.

In use, the pump 10 containing a fluid such as a saline solution is implanted in the scrotal sack of a patient whose penis has implanted therein an appropriate prosthesis, and the connector element 16 is sealed to the prosthesis as known in the art. By situating the pump 10 within the scrotal sack, the patient has convenient access for pump operation. When the patient desires to have a penile erection, he squeezes the first pump component 12 by pinching the scrotal sack. This causes fluid to flow from the first pump component 12 into the first fluid delivery passage 18 and through the first branch 20 thereof for final delivery to the prosthesis through the connector element 16. Fluid travel through the ball valve 24 occurs as the pressurized fluid displaces the ball 25 upwardly and fluid passes there around. Upon cessation of fluid travel, the ball 25 returns to its original seat and closes communication therethrough. As earlier noted, the first pump component 12 is a high-volume, low-pressure component which moves a relatively large amount of fluid into the prosthesis to thereby conveniently reproduce the initial stages of an erection. However, the prosthesis still cannot achieve the desired rigidity because the volume of fluid therein is insufficient. Concurrently, fluid remains in the first pump component 12. To accomplish full deployment of fluid into the prosthesis by using fluid yet remaining in the first pump component, the second pump component 14 is employed. Specifically, by repeatedly squeezing the second pump component 14, residual fluid from the first pump component 12 flows into the first fluid delivery passage 18 and through the second branch 22 thereof for intermediate delivery into the second pump component 14 through the suction valve 26 which operates as known in the art to permit fluid entry. When the second pump component 14 is substantially filled with fluid, and upon continued squeezing, the ball valve 30 opens under pressure created by the high-pressure, low-volume nature of the second pump component 14 to thereby drive the fluid from the second pump component 14 through the second fluid delivery passage 32 and into the connector element 16 for delivery to the prosthesis. This action results in achieving a more natural and complete erection since the amount and pressure of the fluid delivered to the prosthesis provides the rigidity and dimension of which the prosthesis is capable. When the user desires to terminate the erection so obtained, he squeezes the portion of the pump 10 at the site of the ball valve 24 to thereby displace the ball 25. The valve 24 then opens and fluid from the prosthesis rapidly flows therefrom to pass through the first branch 20 of the fluid delivery passage 18 and into the first pump component 12.

While an illustrative and presently preferred embodiment of the invention has been described in detail herein, it is to be understood that the inventive concepts can be otherwise variously embodied and employed and that the appended claims are intended to be construed to include such variations except insofar as limited by the prior art.

What is claimed is:

1. A hand-operable fluid pump apparatus for inflating an inflatable penile prosthesis in communication therewith by pumping fluid thereto, said pump apparatus comprising a high-volume, low-pressure first pump, at least one low-volume, high pressure second pump, and a connector element connectable to said prosthesis, wherein fluid to be pumped to the connector element is housed within the first pump and wherein each of the first and second pumps is in single-valve direct communication with the connector element and in single-valve direct communication with each other.

2. A fluid pump apparatus as claimed in claim 1 wherein the second pump is disposed within the first pump.

3. A fluid pump apparatus as claimed in claim 1 wherein the volume of the first pump is from about 12 cc to about 18 cc.

4. A fluid pump apparatus as claimed in claim 3 wherein the volume of the second pump is from about 2 cc to about 4 cc.

5. A method of inflating an inflatable penile prosthesis, said method comprising:
   a) providing a hand-operable fluid pump apparatus in communication with the prosthesis, said pump apparatus comprising a high-volume, low-pressure first pump and at least one low-volume, high pressure second pump, wherein fluid to be pumped to the prosthesis is housed within the first pump, and wherein each of the first and second pumps is in valved communication with the prosthesis and in valved communication with each other;
   b) repeatedly operating the first pump to thereby deliver fluid therefrom to the prosthesis; and
   c) repeatedly operating the second pump subsequent to operating the first pump to thereby draw remaining fluid from the first pump and deliver said remaining fluid to the prosthesis.

6. The method according to claim 5 wherein the second pump of the pump apparatus is disposed within the first pump thereof.

* * * * *